(12) United States Patent
Lenihan et al.

(10) Patent No.: US 8,206,380 B2
(45) Date of Patent: Jun. 26, 2012

(54) METHOD AND APPARATUS FOR MEASURING CATHETER CONTACT FORCE DURING A MEDICAL PROCEDURE

(75) Inventors: Timothy J. Lenihan, Hradec Kralove (CZ); Robert C. Allison, Rancho Palos Verdes, CA (US); Kenneth L. Carr, Woolwich, ME (US); Peter Van der Sluis, Laguna Beach, CA (US)

(73) Assignee: Advanced Caridiac Therapeutics Inc., Laguna Beach, CA (US)

( * ) Notice: Subject to any disclaimer, the term of this patent is extended or adjusted under 35 U.S.C. 154(b) by 532 days.

(21) Appl. No.: 12/483,407

(22) Filed: Jun. 12, 2009

(65) Prior Publication Data
US 2009/0312754 A1 Dec. 17, 2009

Related U.S. Application Data

(60) Provisional application No. 61/061,305, filed on Jun. 13, 2008.

(51) Int. Cl.
*A61B 18/14* (2006.01)
(52) U.S. Cl. .......................................... 606/33; 606/41
(58) Field of Classification Search .............. 606/27, 606/33, 41
See application file for complete search history.

(56) References Cited

U.S. PATENT DOCUMENTS

| | | | | |
|---|---|---|---|---|
| 5,105,808 | A * | 4/1992 | Neuwirth et al. | 607/138 |
| 5,879,349 | A * | 3/1999 | Edwards | 606/45 |
| 6,210,367 | B1 | 4/2001 | Carr | |
| 6,496,738 | B2 | 12/2002 | Carr | |
| 6,932,776 | B2 | 8/2005 | Carr | |
| 2002/0128636 | A1* | 9/2002 | Chin et al. | 606/16 |
| 2005/0228370 | A1* | 10/2005 | Sterzer et al. | 606/33 |
| 2007/0299488 | A1 | 12/2007 | Carr | |

* cited by examiner

*Primary Examiner* — Michael Peffley
*Assistant Examiner* — Daniel Fowler
(74) *Attorney, Agent, or Firm* — Cesari and McKenna, LLP; John F. McKenna

(57) ABSTRACT

A method for measuring the contact force exerted on tissue by a probe for heating the tissue and containing an antenna which is connected to a radiometer whose output reading indicates the temperature at depth of the tissue contacted by the probe comprises displaying the output reading of the radiometer, applying sufficient power to the probe to heat the tissue to a selected first temperature that is not lethal to the tissue, moving the probe into contact with the tissue, observing the increase in the displayed temperature reading that occurs when the probe contacts the tissue, and advancing the probe toward the tissue until the displayed temperature reading reaches a value corresponding to a selected tissue contact force. After the probe position in the tissue has stabilized, the applied power to the probe may be increased to heat the tissue to a selected second temperature that is lethal to tissue for a sufficient time to ablate the tissue followed by lowering the tissue heating to a sub-lethal temperature. Apparatus for practicing the method is also disclosed.

17 Claims, 8 Drawing Sheets

METHOD AND APPARATUS FOR MEASURING CATHETER CONTACT FORCE DURING A MEDICAL PROCEDURE

RELATED APPLICATION

This application claims the benefit of Provisional Application No. 61/061,305, filed Jun. 13, 2008.

BACKGROUND OF THE INVENTION

This invention relates to a medical antenna catheter apparatus and a method for measuring the contact force applied by an antenna catheter to tissue during a medical procedure.

Our technique may be used any time it is desireable to avoid placing too much force on a medical catheter or the tissue contacted thereby, such as when steering a catheter along a passage in the body or when stabilizing the catheter at a particular location in the body. It is especially advantageous for use during a cardiac ablation procedure. Accordingly, the invention will be described in that context.

Antenna catheters or probes utilize electromagnetic radiation to simultaneously controllably heat, and detect the temperature of, tissue contacted by a catheter or probe. By placing the probe at the region of interest in the body, in this case a target site on the heart, one can treat certain abnormalities, such as a cardiac arrhythmia for example.

Obviously, in order to perform its function, such a probe must be small in diameter and quite flexible and steerable so that it can be threaded into the body to the target site via a natural passage in the body. It may also be required to facilitate various ancillary processes such as display of the target site, cooling or irrigation of the target site, etc.

Antenna probes of the above type are invariably connected by a long cable to an external control unit which includes a transmitter for transmitting electromagnetic energy to the antenna in the probe in order to heat tissue adjacent to the probe, and a receiver in the form of a radiometer which can detect microwave emissions picked up by the probe antenna which emissions reflect the temperature at depth of the tissue adjacent to the probe.

The receiver produces corresponding output signals to control a display which displays the tissue temperature. Those same signals may also be used to control the transmitter to maintain a selected heating profile.

During a typical cardiac ablation procedure, the antenna catheter or probe is used to resistively heat heart tissue usually at the left side of the heart sufficiently to intentionally damage the tissue in order to cure a potentially fatal heart arrhythmia. Typically, heating the tissue to a temperature in excess of 70° C. for 30-60 seconds is sufficient to cause necrosis. This procedure was first attempted over twenty years ago and has become the standard treatment method for most supraventricular tacchycardias (SVTs). It may also be used to treat paroxysmal atrial fibrillation (AF). During treatment, electromagnetic energy, usually in the RF frequency range, is applied between the tip of the antenna probe and a ground plate removably affixed to the patient's back, creating an electrical circuit. The point of highest resistance in this circuit, normally at the interface between the probe tip and the heart tissue, is the region which heats the most and thus may cause irreversible damage to the heart tissue.

In a standard SVT procedure, the heat generated in the tissue contacted by the probe is monitored with a temperature sensor such as a thermister or a thermocouple in the probe tip. A signal from the sensor is applied to a display in the external unit, enabling the operating surgeon to adjust the power as needed to provide sufficient heating of the tissue to cause necrosis, but not enough to result in surface charring of the tissue that could cause a stroke and/or the formation of bubbles (popping) that could rupture the heart vessel wall. The same output from the temperature sensor is sometimes used to provide a feedback signal to the transmitter to achieve controlled heating of the tissue contacted by the probe.

When placing a conventional probe in the heart, it is recognized that the operating surgeon should not press the probe too hard against the tissue. It is fairly well established in the medical literature that the load on the tissue due to the probe should not exceed 0.050 newtons (N), the equivalent of 50 grams of weight. The problem is that the surgeon may not be able to appreciate how much contact force he/she is actually applying to the tissue. This is especially the case if the surgeon is using a robotic system to position the probe and thus has little or no tactile feedback. Indeed, there have been reported cases where the operating physician or robot places too much force on the tissue, causing the probe tip to perforate the heart wall. This condition, known as cardiac perforation, can lead to serious complications including death of the patient.

Also, with experience over time, surgeons have found a need to burn tissue on the left side of the heart increasingly deeper in order to achieve a favorable patient outcome. In order to minimize the above-mentioned surface charring of the tissue, the tips of today's antenna probes may be cooled by circulating a fluid through the probe. However, with this artificial cooling came the undesired consequence that the attending surgeon no longer has the temperature feedback described above because the temperature sensor in the probe no longer takes accurate tissue temperature readings at the point of contact. That is, since the probe tip is being cooled, the temperature sensor in the tip measures the tip temperature, not the tissue temperature.

Another disadvantage of the prior apparatus of this type is the operating surgeon has to work within the radiation field of the antenna catheter during the entire ablation procedure. Such exposure over the years could cause irreparable harm to the surgeon. This may be avoided using robotics allowing for the remote placement of the probe at the target site. However, until now it has proven difficult to control a robotic arm with sufficient accuracy to enable placement of an antenna catheter against the heart tissue with just the right amount of contact force to enable tissue ablation at the point of contact without damaging the heart as described above.

One can envision other medical procedures, e.g. angioplasty, colonoscopy, etc., wherein the movements of a catheter in the body could cause an excessive contact force to be applied to the opposing portions of the tissue and probe resulting in damage to one or both of same.

SUMMARY OF THE INVENTION

Accordingly, this invention aims to provide a method for accurately measuring catheter contact force during placement of a catheter or probe inside a human or animal body.

A further object of the invention is to provide such a method which minimizes the chances of causing tissue damage or catheter damage during placement of a catheter in a body.

Another object of this invention is to provide a method for accurately measuring catheter contact force during cardiac ablation.

Another object of the invention is to provide a method of this type which minimizes the chances of overheating tissue during cardiac ablation.

Yet another of the invention is to provide a method for measuring catheter contact force which is unaffected by cooling of the catheter tip at the point of contact.

A further object of the invention is to provide a method of this type which maximizes the information provided to an operating surgeon or to a robot to assure proper placement of a catheter or probe prior to commencing a medical procedure.

Still another object of the invention is to provide apparatus for implementing the above method.

Another object is to provide apparatus for measuring catheter contact force during placement of a catheter in the body which improves the chances of a favorable patient outcome.

A further object of the invention is to provide apparatus for measuring antenna catheter contact force which can be incorporated easily into a robotic system to allow accurate remote placement of a catheter.

Other objects will, in part, be obvious and will, in part, appear hereinafter.

The invention accordingly comprises the several steps and the relation of one or more of such steps with respect to each of the others, and the apparatus embodying the features of construction, combination of elements and arrangement of parts which are adapted to effect such steps, all as exemplified in the following detailed description and the scope of the invention will be indicated in the claims.

In general, the present apparatus comprises an antenna catheter or probe for insertion into a human or animal patient. The probe may be connected by a cable to an external control unit which may include a transmitter, a receiver, preferably in the form of a radiometer, and a temperature display.

While we will specifically describe the invention as used in cardiac ablation, the invention may also be used in other ablation procedures such as the treatment of BPH, cancer and the like.

In accordance with our method, during an ablation procedure, the temperature at depth in the tissue contacted by the antenna catheter is measured by microwave radiometry and used to determine the catheter contact force on the tissue. This is possible because we have found that there is a strong correlation between the two, even if the antenna catheter is being cooled. In addition, because microwave radiometry measures a volumetric temperature, it is independent of the angle of contact of the probe to the tissue, unlike conventional temperature probes incorporating thermistors and thermocouples which only measure a point.

More particularly, we have found that when a low (sub-lethal) amount of energy, or a higher amount of energy for a short time, is applied to the antenna in the probe and the output reading of the apparatus' radiometer is observed as the probe approaches and contacts the target tissue, the radiometer reading is a reliable indicator of 1) tissue contact and 2) the force exerted on the tissue by the probe.

That being the case, a surgeon may observe the apparatus' radiometer or temperature reading as the probe approaches and contacts the heart tissue. When contact is achieved, 1) there is a noticeable rise in that reading and 2) thereafter the reading increases in relation to the contact force. Thus, using a suitable temperature/force calibration table or with proper programming and formatting of the display, the surgeon can see directly the actual amount of catheter contact force being exerted on the tissue at any given time. This is very important during the placement of a catheter into the heart, especially when a robotic system is being used to position the probe and the physician has lost all tactile feel as described above.

When the desired force is achieved and the catheter or probe has safely reached the desired place in the heart, the power to the antenna in the probe may be increased to a higher level for a sufficient time to effect a lethal temperature rise in the tissue, i.e. >70° C., and thus the actual ablation.

Using the force information during placement and subsequently the temperature information during lethal ablation, the surgeon can assuredly reach the correct place in the heart without causing a perforation or other damage to heart structures and then ablate the tissue at the point of contact without causing surface charring or the formation of bubbles in the tissue.

During both the placement of the catheter and the subsequent lethal ablation, cooling fluid may be conducted to the catheter and either circulated back from the instrument (closed circuit) or allowed out of the catheter through small holes therein (open irrigation). In the case of the placement part of the procedure prior to lethal ablation, fluid may be flowed to the catheter simply to ensure that the fluid path remains open and does not become clogged. Since this is the only purpose of the flowing fluid, the flow rate may be quite low, e.g. 2 cc/min. Then, during the ablation part of the procedure, the flow rate may be increased to aggressively cool the surface of the tissue to prevent tissue charring or overheating. In this case, the flow rate may range from a low setting of 5 cc/min. to a high of 40 cc/min.

In either case, while fluid is flowing to the catheter, conventional temperature probes such as those incorporating thermocouples and thermistors would be greatly influenced by the temperature of the cooling fluid. However, with the present probe, the safe placement in, and ablation of, the heart or other tissue as mentioned above is essentially independent of the temperature of the catheter tip itself due to such artificial cooling because microwave radiometry measures the tissue temperature at depth and is a function of the three-dimensional antenna pattern produced by the probe.

Obviously the same tissue temperature signal from the radiometer may be used to help control the movements of a robotic arm to properly position the probe when the ablation procedure is being performed remotely. That is, while the ablation is being carried out, a set power should give a fixed tissue temperature rise for a given applied contact force. Therefore, just like during a manual probe placement, using a suitable calibration table or with proper programming and formatting of the display, the surgeon can see the amount of catheter contact force being exerted by the robotic probe on the tissue at any given time during the ablation procedure.

BRIEF DESCRIPTION OF THE DRAWINGS

For a fuller understanding of the nature and objects of the invention, reference should be made to the following detailed description taken in connection with the accompanying drawings, in which.

DESCRIPTION OF A PREFERRED EMBODIMENT

Figure 1:
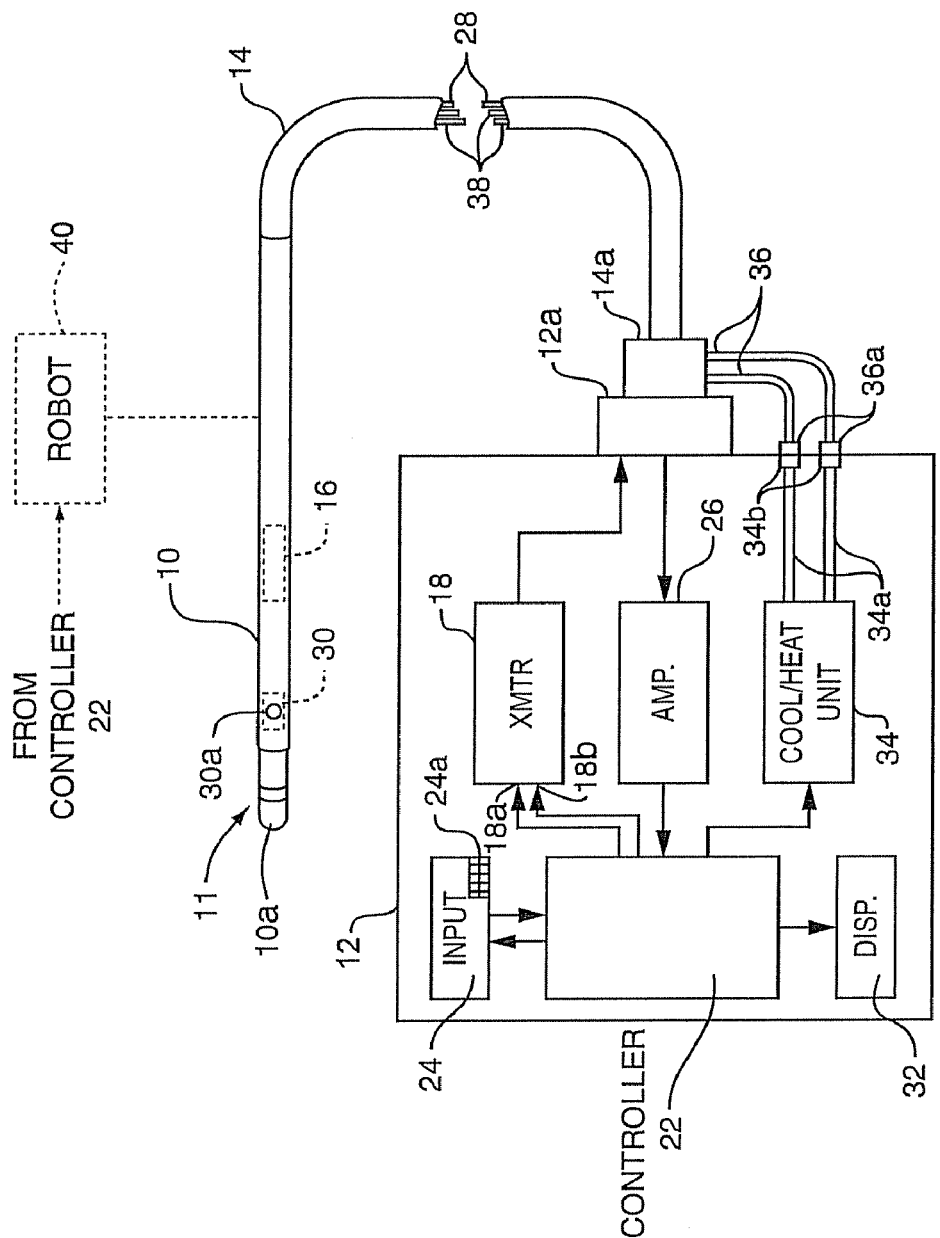
FIG. 1 is a diagrammatic view of cardiac ablation apparatus incorporating the invention.

Referring to FIG. 1 of the drawings, the apparatus for carrying out the invention comprises a minimally invasive, steerable antenna catheter or probe 10 containing an antenna 11 and an external control unit 12. The probe is adapted to be threaded into a patient via a natural or incised passage in the patient's body. The probe is connected to unit 12 by a flexible cable 14 having an end connector 14a that joins a mating connector 12a on unit 12. Typically, catheter 10 may be only 10 to 12 mm long and 2 mm in diameter. Preferably, catheter 10 has a built-in radiometer 16 and is of the type disclosed in US2007/0299488 A1, the entire contents of which is hereby incorporation by reference herein.

The control unit 12 may include a transmitter 18 which delivers power to probe 10 by way of cable 14. The output signal from transmitter 18 has a frequency that is different from, and preferably much lower than, the frequency of the radiometer 16 which may operate at a center frequency of, say, 4 GHz. The illustrated transmitter has an output in the RF frequency range, i.e. below 300 mHz, most preferably 500 kHz, so that cable 14 does not have to be a coaxial cable, thereby enabling it to be more flexible and less lossy than a coaxial cable. Transmitter 18 is controlled by a programmable controller or processor 22, which receives instructions via control buttons 24a on an operator control panel 24 in unit 12.

The control unit 12 also includes an amplifier 26 which receives a temperature-indicating output signal or reading from radiometer 16 via conductors 28 in cable 14. Amplifier 26 conditions that signal and routes it to controller 22 which delivers a corresponding control signal to an input 18a of transmitter 18 causing transmitter 18 to deliver enough power to the antenna 11 in catheter 10, e.g. 20-30 watts for 30-60 seconds, to cause ablation of the tissue contacted by the catheter tip 10a.

Controller 22 differs from the one in the aforesaid patent publication in that it can deliver a second control signal to an input 18b of transmitter 18 which causes the transmitter to transmit a relatively low amount of power, e.g. less than 5 watts, or a higher wattage for a short period of time, e.g. 30 watts for 5-10 seconds, to antenna 11 that will cause a non-lethal in-depth temperature rise, e.g. up to 5° C., of the tissue opposite the catheter tip 10a. For this, a three position switch 30 with a control button 30a on probe 10 may be connected via cable 14 to the controller 22 in unit 12. When the button 30a is not depressed, transmitter 18 applies no power to catheter or probe 10. When that button is depressed half way, the controller instructs the transmitter via input 18b to apply the non-lethal low power (or higher power for short time) to probe 10. When the button 30a is depressed all the way, the controller instructs the transmitter via input 18a to apply lethal power to the probe for a selected time.

The controller 22 may also apply the amplified temperature-indicating signal or temperature reading from the radiometer to a display 32 which may thereupon display at any time the temperature at depth of the tissue being probed by catheter 10. Preferably, but not necessarily, the display 32 also displays catheter contact force directly as a function of the radiometer reading so that the surgeon can see an indication of that force in real time. Of course, display 32 can also display other parameters relating to the proper operation of the apparatus such as transmitter output power, reflected power, elapsed time, etc.

The control unit 12 may also include a cooling unit 34 controlled by controller 22 and connected via hoses 34a, 34a to fittings 34b, 34b. Those fittings are coupled to fittings 36a, 36a of a pair of hoses 36 leading to connector 14a. That connector is connected to catheter 10 via passages 38 in cable 14, enabling the flow of cooling fluid to catheter 10, all as described in the above patent publication. As noted above, such closed circulation catheter cooling is sometimes used to prevent surface charring and bubble formation during ablation. As also mentioned above, the catheter tip may have small holes (not shown) to permit open irrigation.

For remote operation, catheter or probe 10 may be positioned by a robot indicated in phantom at 40 having an arm 40a attached to the probe, in which case the robot may also receive the temperature signal or reading from radiometer 16 via controller 22 to help position the probe to apply the desired force, not to exceed the equivalent of 50 grams, to the tissue at the point of contact therewith.

Figure 2:
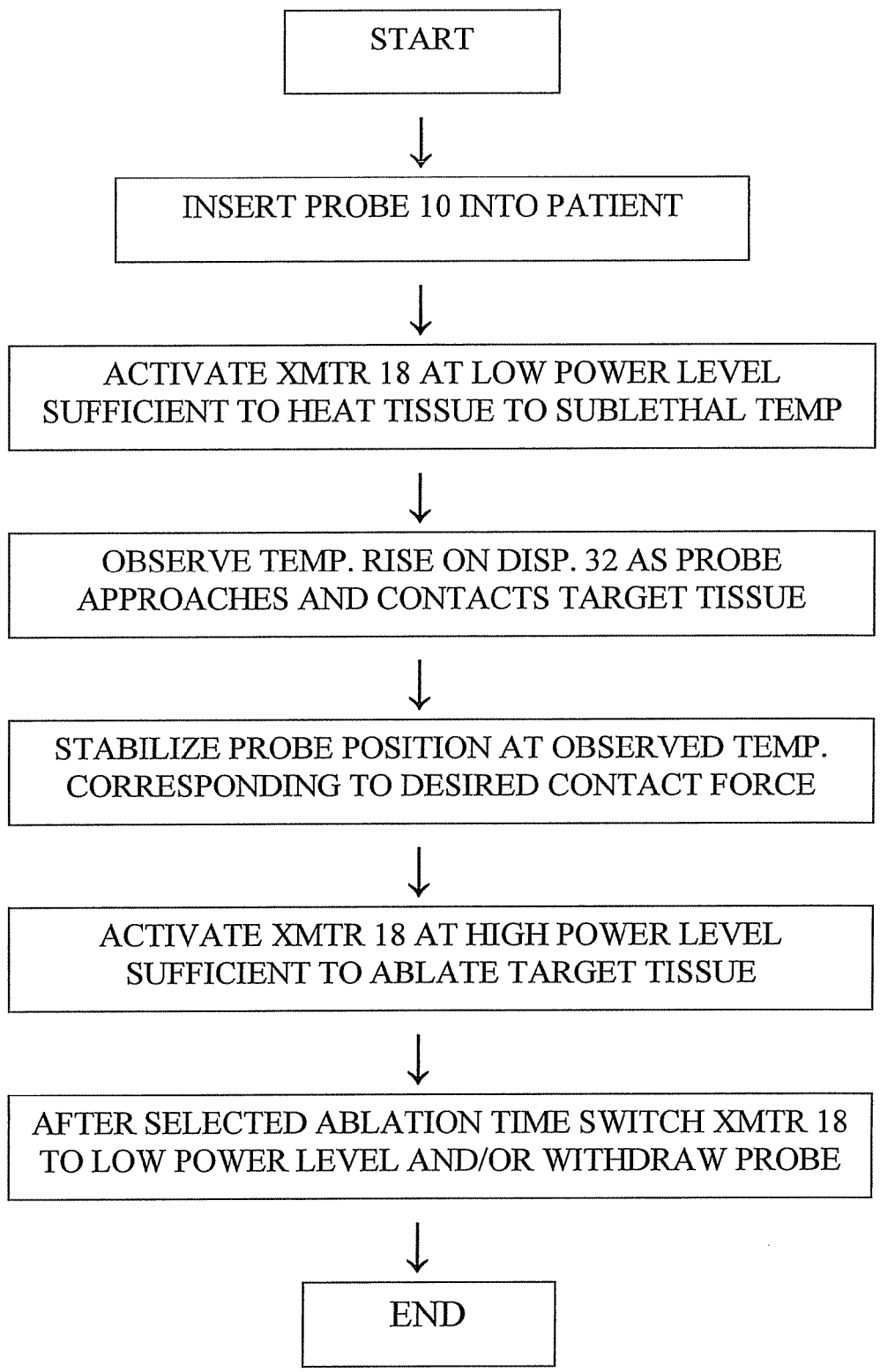
FIG. 2 is a block diagram showing the steps for carrying out the method using the FIG. 1 apparatus.

FIG. 2 shows how the FIG. 1 apparatus may be used to practice our method.

Working Example 1

A test was performed to determine if there is a power level which keeps the temperature rise in tissue below 5° C. at full contact but causes enough of a temperature rise in the radiometer output signal or reading to accurately determine the contact force applied to the tissue.

Testing was performed with the delivery of low power, i.e. 0, 1, 2 and 4 watts, to the antenna in the catheter and the catheter was attached to a force sensor. The catheter tip was positioned 2-3 mm above the target tissue and then moved slowly until it reached the tissue and then moved into the tissue.

Figure 3:
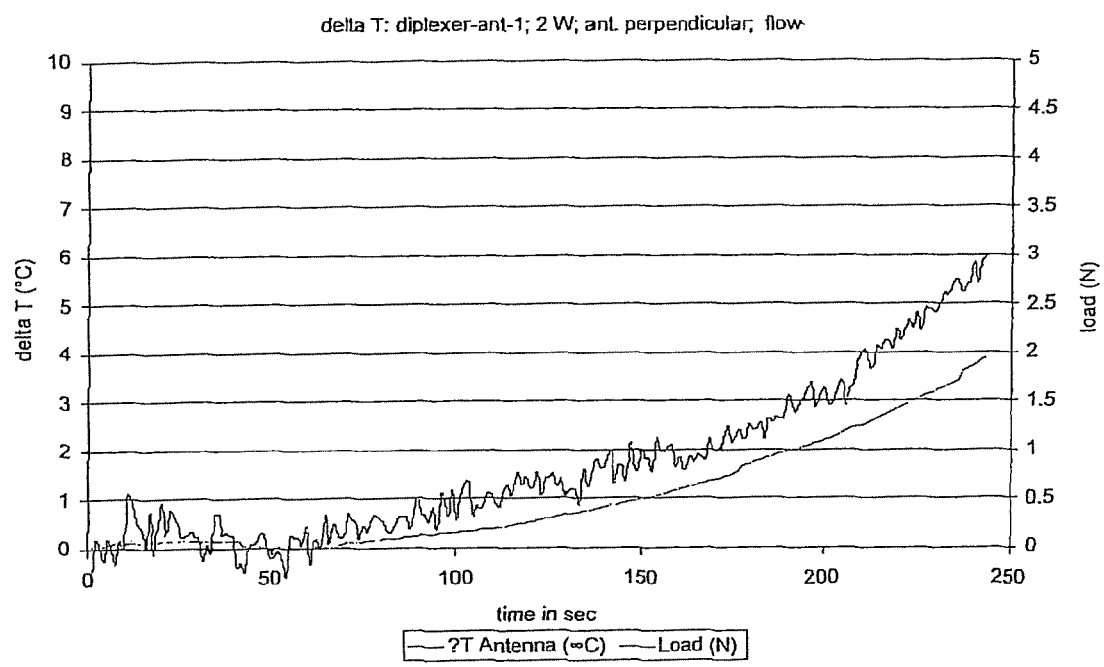
FIG. 3 is a graphical diagram showing the FIG. 1 apparatus' radiometer reading and probe contact force (tissue load) over time for a 2 watt test run.

FIG. 3 graphs a typical "2 watt" run using our method, recording the force exerted by the probe on the tissue and the radiometer reading while 2 watts of power were applied. As shown in FIG. 3, the radiometer reading indicated the beginning of a temperature rise as the probe touched the tissue at time 50 seconds and the temperature rise clearly tracked the increase in force exerted on the tissue over time.

Figure 4:
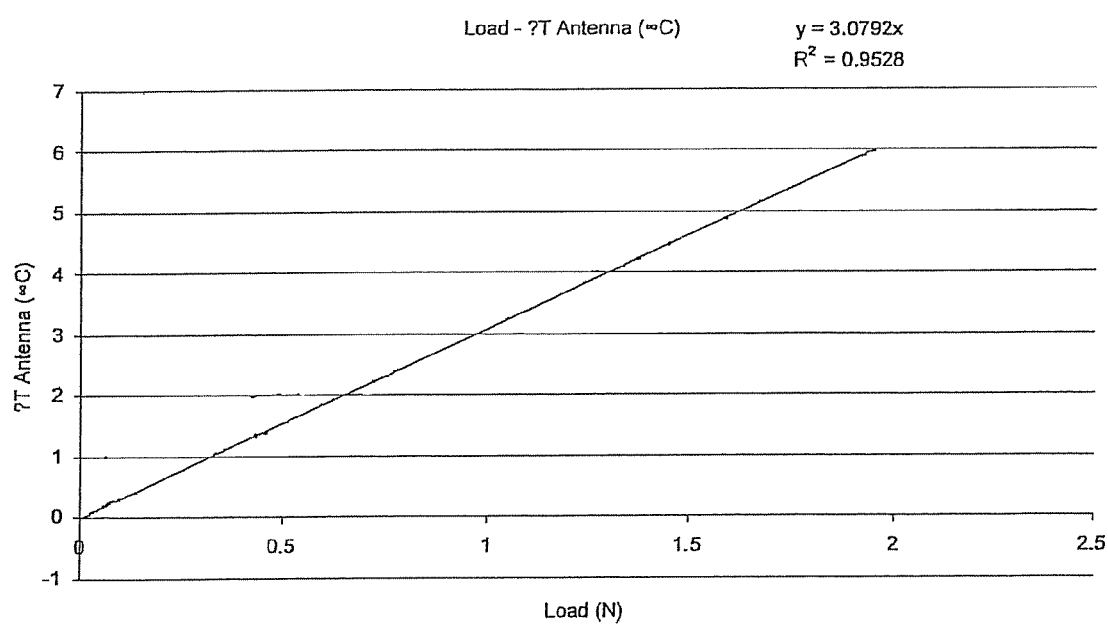
FIG. 4 is a graphical diagram showing the radiometer reading versus the probe contact force (tissue load) for the 2 watt run.

FIG. 4 is a plot of the radiometer reading vs. probe contact force on the tissue during the 2 watt run, indicating a strong correlation between the two. This evidences that when a low power level is applied over time to the probe antenna, the radiometer reading is a reliable indicator of actual tissue contact by the probe as well as of the force exerted on the tissue by the probe after such contact.

Working Example 2

A second test was performed to determine if there is a high power level but short time which keeps the temperature rise in tissue below 5° C. at full contact, but causes enough of a temperature rise in the radiometer to accurately determine the contact force applied to the tissue.

Testing was performed with the delivery of high power, i.e. 30 watts, for a short period of time, i.e. 10 and 5 seconds, to the antenna in the catheter and the catheter was attached to a force sensor. The catheter tip was positioned 2-3 mm above the target tissue and then moved slowly until it reached the tissue and then moved into the tissue. The antenna was stopped when the load on the tissue was 5 grams and then high power was pulsed on for 10 seconds. This was repeated for every 5 gram increment until 50 grams, which is thought to correspond to the maximum allowable force which should be exerted on the heart tissue.

Figure 5:
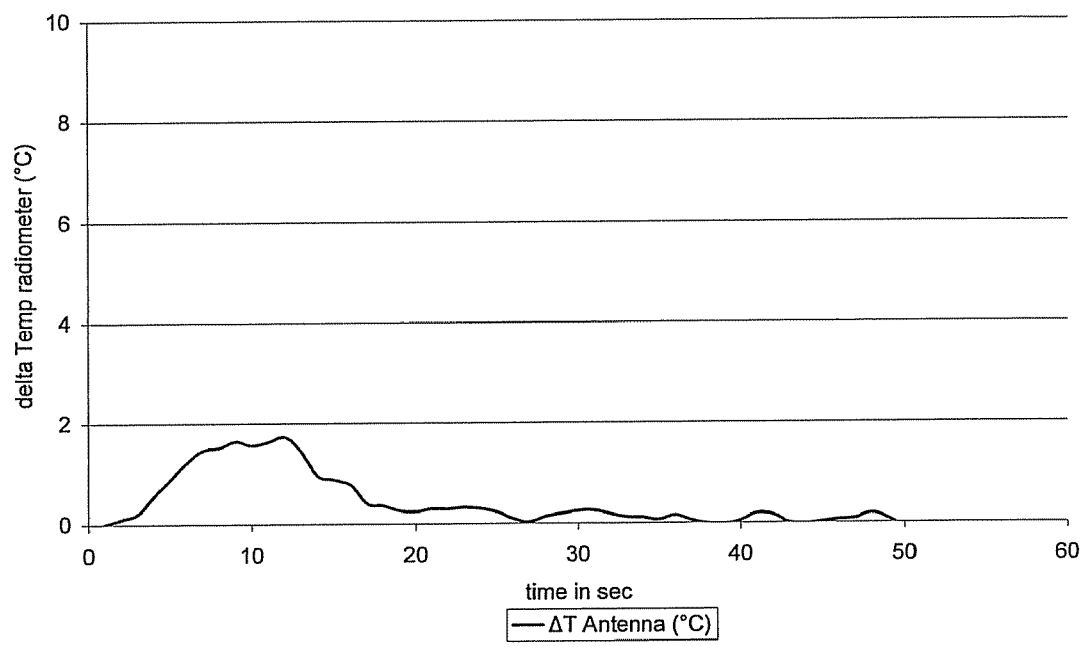
FIG. 5 is a graphical diagram showing the radiometer reading over time for the case where a weighted probe places a 5 gram load on the tissue.
Figure 6:
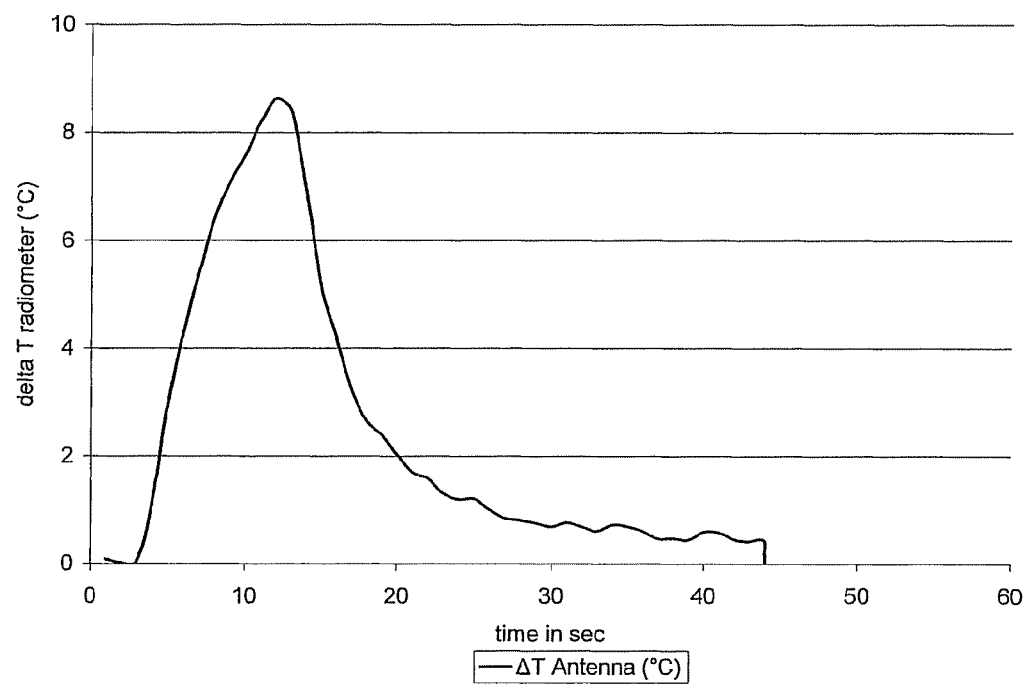
FIG. 6 is a graphical diagram showing the radiometer reading over time for the case where a weighted probe places a 50 gram load on the tissue.

FIG. 5 shows an example of the temperature rise in the radiometer during a 10 second application at 30 watts when the tissue was under a 5 gram probe contact load. FIG. 6 shows an example of the temperature rise in the radiometer during a 10 second application at 30 watts when the tissue was under a 50 gram load. The 50 grams obviously cause a significantly higher temperature response in the tissue and thus a higher temperature rise as recorded by the microwave radiometer.

In order to correlate the temperature rise to contact force or tissue load in this case, one can use the maximum temperature rise as recorded by the radiometer or the slope of the temperature rise. In either case, the data shows that there is a correlation of the temperature rise to contact force or tissue load in this high temperature, short time, case.

Figure 7:
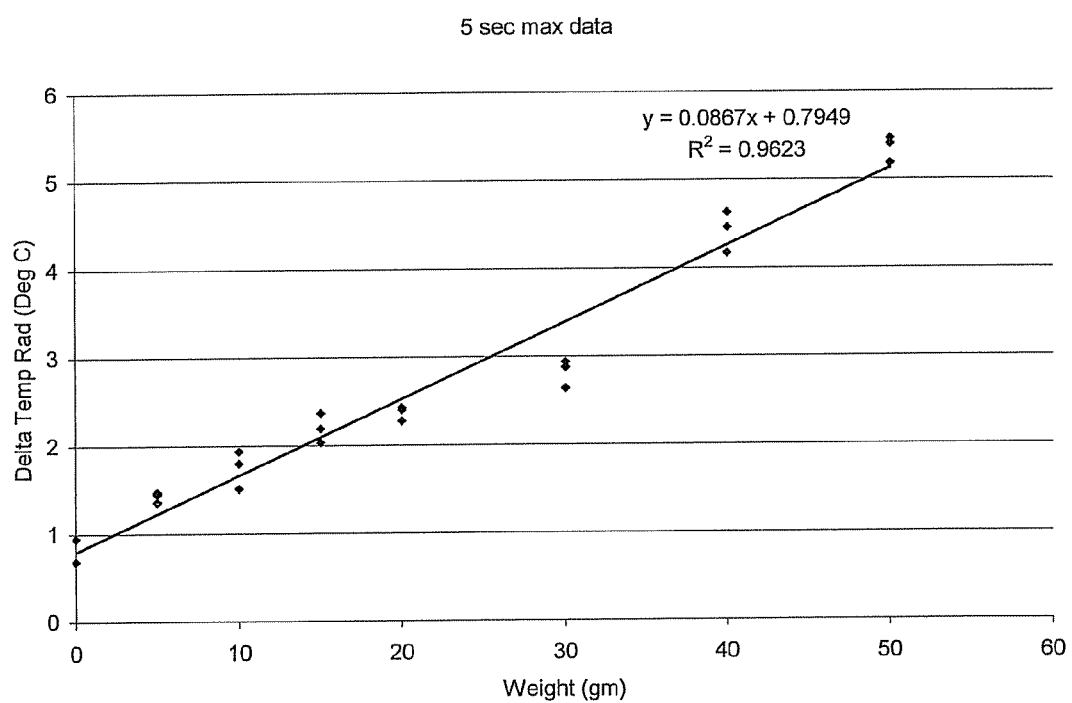
FIG. 7 is a graphical diagram showing the change in the radiometer reading in 5 seconds versus the load on the tissue for numerous test runs.
Figure 8:
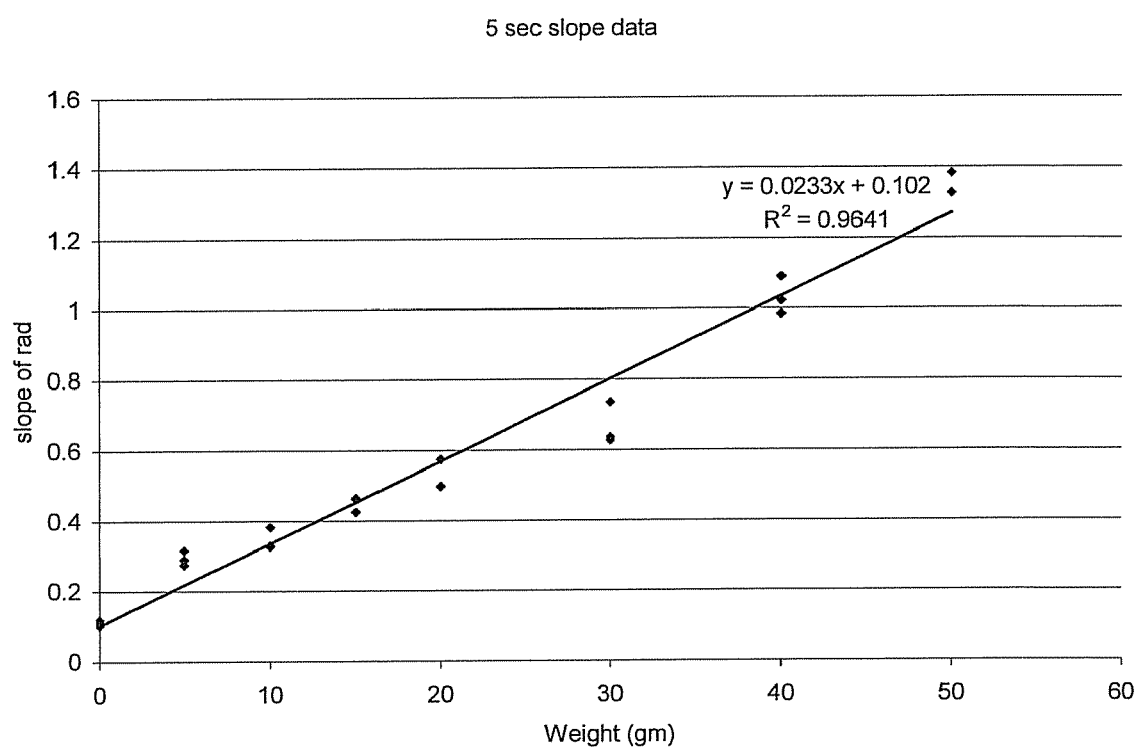
FIG. 8 is a graphical diagram showing the slope of the radiometer reading in 5 seconds for those test runs.

FIGS. 7 and 8 plot tissue load vs. maximum temperature rise in 5 seconds and vs. the slope in the first 5 seconds, respectively, for the antenna power mentioned above, i.e. 30 watts. In both cases, there is a strong correlation to the probe contact force or tissue load.

To practice our invention, in accordance with FIG. 2, the probe 10 is inserted into a patient close to the target tissue, e.g. the left side of the heart. Then, by depressing control button 30a half way, the surgeon causes controller 22 to control the transmitter 18 so that the transmitter applies low, sub-lethal, power to antenna 11 in probe 10. While observing the temperature reading, or more preferably a force reading, on display 32, the surgeon may move the probe until its tip 10a actually contacts the heart tissue. This event will be marked by an observable increase in the temperature and/or contact force (tissue load) reading on the display, as shown, for example, at time 50 seconds in FIG. 3.

As the probe tip is moved into the tissue, the temperature and/or contact force reading will increase and the probe position may be stabilized when the observed temperature (or force) reading indicates the desired contact force. As noted above, that desired force should not exceed the generally acceptable equivalent weight limit of 50 grams. At this point, the surgeon may depress control button 30a on probe 10 all the way, causing the controller to instruct the transmitter 18 to apply the selected lethal power to probe antenna 11. At this time, the probe tip may be cooled as described above to prevent surface charring of tissue.

After a sufficient time to cause ablation of the tissue at the point of contact, the control button 30a may be released so that controller 22 switches the transmitter 18 to its low power level or to OFF so that the probe can be moved to a different contact point on the target tissue and the process repeated. Of course the tissue may be cooled to a sub-lethal temperature simply by withdrawing the heated probe from the tissue.

It will thus be seen that the objects set forth above, among those made apparent from the preceding description, are efficiently attained. Also, certain changes may be made in carrying out the above method and in the construction set forth without departing from the scope of the invention. For example, during probe placement, the tissue may be heated by a resistive heating element positioned in the probe tip and connected to a current source instead of by power applied to the antenna 11. In this event, cooling fluid should not be delivered to the probe. Also, when the probe contacts the tissue as described above, the force exerted on the tissue by the probe is equal to the force exerted on the probe by the tissue. Therefore, the invention may be used to prevent damage to a probe tip that is especially fragile. Therefore, it is intended that all matter contained in the above description or shown in the accompanying drawings shall be interpreted as illustrative and not in a limiting sense.

It is also to be understood that the following claims are intended to cover all of the generic and specific features of the invention described herein.

What is claimed is:

1. A method for measuring the contact force exerted on tissue by a probe capable of heating tissue and containing an antenna connected to a radiometer whose output reading indicates the temperature at depth of the tissue contacted by the probe, said method comprising the steps of:
   displaying the temperature reading of the radiometer;
   applying sufficient power to the probe to heat the tissue to a selected first temperature that is not lethal to the tissue;
   moving the probe into contact with the tissue;
   observing the increase in the temperature reading that occurs when the probe actually contacts the tissue, and
   advancing the probe toward the tissue until the temperature reading reaches a value corresponding to a selected tissue contact force.

2. The method defined in claim 1 including the additional steps of
   after the probe position in the tissue has stabilized, increasing the applied power to the probe sufficiently to heat the tissue to a second, higher, temperature that is lethal to the tissue for a sufficient time to ablate the tissue, and
   following said tissue ablation, cooling the tissue to a sub-lethal temperature.

3. The method defined in claim 1 wherein the probe is powered by supplying electromagnetic energy to the antenna.

4. The method defined in claim 1 wherein the probe is powered by supplying electrical current to a heating device in the probe.

5. The method defined in claim 1 wherein said moving and advancing steps are accomplished manually.

6. The method defined in claim 1 wherein said moving and advancing steps are accomplished by a robotic arm attached to the probe.

7. The method defined in claim 1 including the additional step of displaying, at least during the moving and observing steps, the force exerted on the tissue by the probe as a function of the temperature reading.

8. The method defined in claim 2 wherein the cooling step is accomplished by withdrawing the probe from the tissue.

9. The method defined in claim 2 wherein the cooling step is accomplished by reducing the heating of the probe below said second temperature.

10. The method defined in claim 2 including the additional step of flowing a cooling fluid to the probe at least while the probe is heated to the second temperature.

11. Apparatus for measuring the contact force exerted on tissue by a probe, said apparatus comprising
    a probe containing an antenna, said antenna being connected to a radiometer which produces an output reading corresponding to the temperature at depth of the tissue contacted by the probe;
    a moving mechanism for moving the probe relative to the tissue;
    a display device responsive to said output reading for displaying the tissue temperature;
    a heating device in the probe for heating the tissue, and
    a heating controller responsive to said output reading for controlling the heating device, said heating controller including a temperature/force calibration table, and being programmed to control the heating device so as to heat the probe to a selected first temperature which is not lethal to the tissue, and control the moving mechanism to advance the probe toward the tissue whereby the display device first displays the sudden increase in the output reading that occurs when the probe actually contacts the tissue followed by a gradual output reading increase that occurs as the probe is advanced further into the tissue and then stop the advance when the gradual output reading increase reaches a value corresponding to a selected tissue contact force indicated by said calibration table.

12. The apparatus defined in claim 11 wherein after said further advance is stopped, the controller is programmed to control the heating device to thereafter heat the tissue to a selected second temperature that is lethal to the tissue for a sufficient time to ablate the tissue.

13. The apparatus defined in claim 11 wherein the heating device includes said antenna and further including an RF generator connected to the antenna.

14. The apparatus defined in claim 11 wherein the heating device includes a heating element in the probe and further including a current source connected to the heating element.

15. The apparatus defined in claim 11 wherein said moving mechanism includes a robot which is attached to the probe and limits the further advance of the probe into the tissue as a function of said gradual output reading increase.

16. The apparatus defined in claim 11 wherein the display device also displays the tissue contact force as a function of said output reading.

17. The apparatus defined in claim 12 and further including a cooling device for flowing a liquid to the probe to cool the probe below said second temperature.

* * * * *